United States Patent [19]
Fedorov et al.

[11] Patent Number: 5,258,025
[45] Date of Patent: Nov. 2, 1993

[54] CORRECTIVE INTRAOCULAR LENS

[76] Inventors: Svyatoslav N. Fedorov, pereulok Dostoevskogo, 1/21, kv. 32; Viktor Zuev, ulitsa Ermolovoi, 17, kv. 27; Bulat M. Aznabaev, ulitsa Onezhskaya, 7, korpus 16, kv. 64, all of Moscow, U.S.S.R.

[21] Appl. No.: 884,246

[22] Filed: May 11, 1992

Related U.S. Application Data

[63] Continuation of Ser. No. 632,162, Dec. 21, 1990, abandoned.

[30] Foreign Application Priority Data

Nov. 21, 1990 [SU] U.S.S.R. ................. 4881670

[51] Int. Cl.$^5$ ............................................. A61F 2/16
[52] U.S. Cl. ............................................. 623/6
[58] Field of Search ............................................. 623/6

[56] References Cited

U.S. PATENT DOCUMENTS

| 2,834,023 | 5/1958 | Lieb | 623/6 |
| 4,254,509 | 3/1981 | Tennant | 623/6 |
| 4,585,456 | 4/1986 | Blackmore | 623/6 |
| 4,664,666 | 5/1987 | Barrett | 623/6 |
| 4,737,322 | 4/1988 | Bruns et al. | 623/6 |
| 4,769,035 | 9/1988 | Kelman | 623/6 |
| 4,840,627 | 6/1989 | Blumenthal | 623/6 |

FOREIGN PATENT DOCUMENTS

| 1103399 | 11/1955 | France | 623/6 |
| 8902252 | 3/1989 | World Int. Prop. O. | 623/6 |

OTHER PUBLICATIONS

"The Choyce Mark VIII and Mark IX anterior chamber implants", Choyce, AM Intra-Ocular Implant Soc. J., vol. V, Jul. 1979, pp. 217-221.

*Primary Examiner*—Randy C. Shay
*Attorney, Agent, or Firm*—Burgess, Ryan & Wayne

[57] ABSTRACT

An optical body, a positioning element, and a supporting element are shaped as an integral unit and have the same radius of curvature that provides for full adherence of the integral unit to an intact natural lens. The distance between the diametrically opposite portions of the supporting element is at least equal to the distance between Zinn's zonules on which the corrective lens rests.

3 Claims, 2 Drawing Sheets

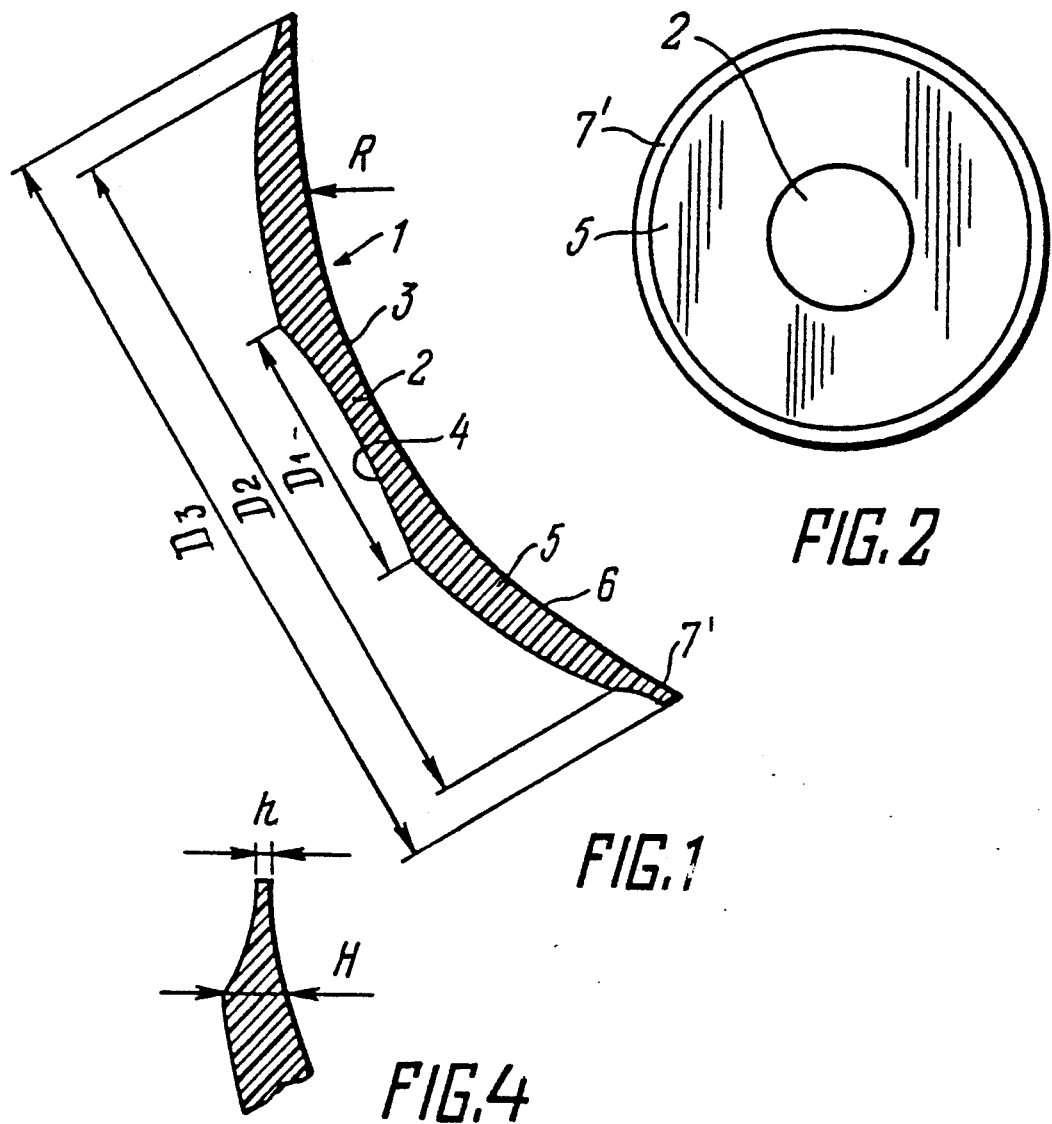

CORRECTIVE INTRAOCULAR LENS

This application is a continuation of application Ser. No. 632,162, filed Dec. 21, 1990, abandoned.

BACKGROUND OF THE INVENTION

1. Field of the Invention

The present invention relates generally to medicine, more specifically to ophthalmology and has particular reference to a corrective intraocular lens which can find successful application for, e.g., treatment of myopia, hyperopia, astigmatism, and some other eye diseases.

2. Description of the Prior Art

Correction of such eyesight deficiences as myopia, hyperopia, and the like has involved the use of glasses or contact lenses. However, correction with the use of such devices is but a temporary one, since such devices must be placed and removed periodically, e.g., while skiing, swimming, etc.

Permanent correction of eyesight is performed with the aid of keratotomy, one of whose techniques includes removal of the corneal layer and its reshaping, while another technique consists in making a multiplicity of radial cuts into the corneal layer to adjust the curvature thereof, followed by healing. The aforesaid kerato-refractive surgical techniques are of the irreversible nature and suffer from inadequate accuracy of prognostication of the postoperative refractive effect.

Intraocular lenses or lenticuli have been used to solve these problems, but they are intended largely for correction of postcouching aphakia.

There has been provided a corrective lens for use in conjunction with the intact natural lens, such as that described in U.S. Pat. No. 4,585,456 issued on Apr. 29, 1986 to Blackmore. Said corrective lens employs an optical body formed of material biocompatible with the eye and having a concave posterior surface whose curvature suits that of the external surface of the natural lens. The aforesaid optical body includes a means for its positioning so as to be adjacent to the natural lens. To retain the corrective lens in said position provision is made for supporting elements shaped as e.g., open loops associated with the positioning means as is known in the art with respect to intraocular lenses. When inserting such a corrective lens within the patient's eye the supporting elements are placed in the ciliary sulcus. However, such an attachment is subject to all disadvantages inherent in fastening of an intraocular lens in the ciliary sulcus, in particular, the danger, and rather frequent, of inflammations of the ocular tissues. Moreover, as it has been confirmed by practical experience, such an attachment might be inadequately reliable and results in dislocation or displacement of the corrective lens.

SUMMARY OF THE INVENTION

It is an object of the present invention to provide a corrective lens whose supporting element ensures stable attachment in the patient's eye and reduces the danger of postoperative complications.

This object is accomplished by providing a supporting element which establishes an integral unit with the positioning element, is situated along the periphery of the latter and features the same curvature of its surface as viewed from the posterior surface of the optical body, while the distance between the diametrically opposite free ends of the supporting element is at least equal to the distance between the diametrally opposite the ciliary (Zinn's) zonule, and the supporting element is thinner than the positioning element.

It is due to the use of the aforesaid geometric parameters that any interaction with the sensitive portions of the ocular tissues is prevented, whereby the danger of postoperative inflammations due to contacting of the supporting element with the ocular tissues is drastically reduced if not completely ruled out. The Zinn's zonules or ligaments are strong enough to hold the supporting element and hence the entire corrective lens in the required position which is preset during surgery. It should be borne in mind that in this case good matching of the optical body with the natural lens is achieved.

The supporting element may be shaped as an annular thinned extension to the positioning element, or as four local projections arranged in pairs symmetrically and diametrally opposite to each other, the latter variant being a preferred one, since it makes possible some reduction of the overall dimensions of the corrective lens.

Thinning is expedient to be made due to reduction of thickness on the side of the outer surface along a curvilinear generant.

A special method for implantation of a corrective lens is proposed.

BRIEF DESCRIPTION OF THE DRAWINGS

In what follows the invention is illustrated in a detailed description of some specific exemplary embodiments thereof representing the proposed corrective lens to be read in conjunction with the accompanying drawings, in which:

FIG. 1 is a sectional view of a corrective lens, according to the invention, intended for use in a phakic eye;

FIG. 2 is a plan view of an embodiment of the corrective lens, according to the invention;

FIG. 4 is a scaled-up view of the thinned portion of the positioning element.

DESCRIPTION OF THE PREFERRED EMBODIMENTS

Figure 3:
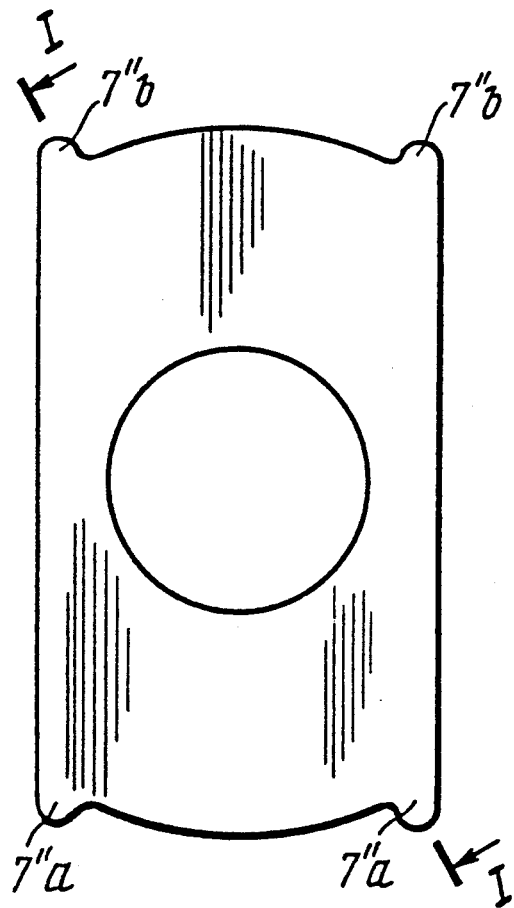
FIG. 3 is a plan view of an alternative embodiment of the corrective lens, according to the invention.

Now referring first and foremost to FIG. 1 one can see a sectional view of the proposed corrective lens indicated as a whole with Ref. No. 1 and intended for correction of a phakic eye. Such a lens can be produced by molding from such a material as polymethylmethacrylate, silicone rubber, polyhydroxethyl-methacrylate, the copolymer of silicone and methylmethacrylate, polyvinylpyrrolidone, and other materials which are biocompatible with the ocular tissue and aqueous humor and preferably hydrophilic and/or permeable to oxygen.

A corrective lens 1 has an optical body 2 featuring a biconcave surface, a posterior surface 3 and an anterior surface 4. The posterior surface 3 is located on the side that should adhere to the outer surface of the natural lens and has a radius R of curvature corresponding to the radius of curvature of the outer surface of the natural lens as it will be described in more detail hereinafter with reference to FIG. 4. As a matter of fact the radius of curvature ranges between 9 and 11 mm, while the optical body diameter $D_1$ falls within 4 and 6 mm.

The optical body 2 is encompassed, along the entire circumference, by a positioning element 5, wherein the radius of curvature of its posterior concave surface 6 equal to the radius R of the posterior surface 3 of the optical body 2. The positioning element 5 serves for setting the optical body 2 in the eye on the outer surface of an intact natural lens in the course of orienting of the optical body with respect to the natural lens. Diameter $D_2$ of said positioning element ranges within about 10 mm to about 10.5 mm.

A supporting element is made integral with the positioning element and may have diverse configurations as in plan.

For instance, in an embodiment shown in FIG. 2 a supporting element 7' is annular-shaped, while in an embodiment illustrated in FIG. 3 the supporting element is formed by two pairs of diametrically opposite projections 7'a and 7"b. As is evident from FIG. 3 the projections are bevelled along parallel chords. Thus, the supporting elements are located at places of intersection of the chords with the circumference.

Incidentally, in any case the supporting element is thinned as compared with the positioning element 5, as can be seen well from a sectional view of FIGS. 1 and 4. Thus, with the thickness H of the supporting element equal to 0.1 mm the thickness h of said element at its peripheral surface is within 0.01 and 0.05 mm. However the edge of the supporting element must not be excessively sharp for fear of injuring the eye tissue with said edge. Taking account of the fact mentioned above said thinning is expedient to be made along a curvilinear generant on the side of the anterior surface of the supporting element. The posterior surface of the supporting element has the same radius of curvature as the posterior surface of the supporting element 2. The distance $D_3$ between the diametrically opposite ends of the supporting element must not be less than the diametral distance between the Zinn's zonules or Zinn ligaments 10 (FIG. 5) and as a rule ranges between 11.5 mm and 12.0 mm.

The proposed corrective lens is positioned as follows.

Figure 5:
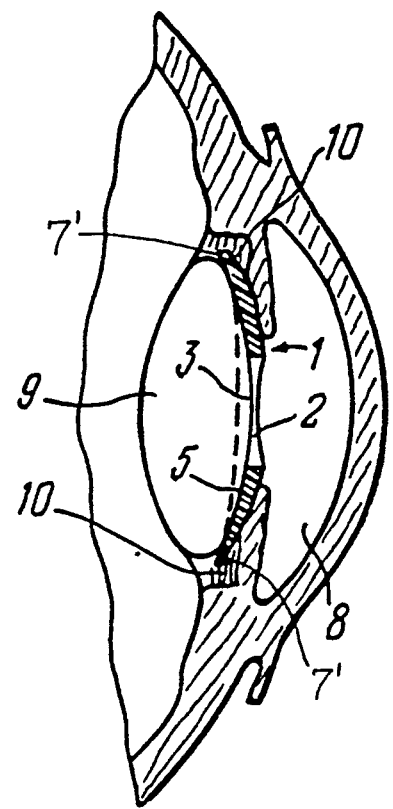
FIG. 5 is a sectional view of an eyeball showing the corrective lens, according to the invention, inserted therein.

Under local anesthesia an incision into the cornea or limbus is made to establish an access to an anterior eye chamber 8 (FIG. 5). Then the corrective lens 1 is introduced, using a forceps, through the preliminary dilated pupil, into the posterior eye chamber at 6 o'clock, then at 12 o'clock. Next the corrective lens 1 is adjusted for position by moving it with its setting surface 5 over the outer surface of an intact natural lens 9, while attempt is made to attain such a position at which the optical body 2 be arranged on the eye optic axis and the posterior surface 3 of the optical body 2 be adjacent to the outer surface of the natural lens and the supporting element gets onto the Zinn's zonules, where said element is held in place on the system of the Zinn's zonules. On completion of surgery the operative incision is stitched up.

While a preferred embodiment of the invention has been disclosed herein, it will be understood that various modifications and versions may occur to those skilled in the art, e.g., a biconcave optical body may be replaced with a concavoconvex or toroidal optical body, such modifications and versions not departing from the spirit and scope of the present invention as defined by the claims that follow.

What is claimed is:

1. An intraocular lens comprising:
   an optical body posterior concave surface with a curvature,
   an optical body anterior surface, and
   an optical body periphery,
   a positioning element in surrounding relation to the optical body and connected to the periphery of the optical body, said positioning element including:
     a positioning element periphery, and
     a positioning element posterior concave surface that forms a smooth continuation of said optical body posterior concave surface and which has a curvature identical to the curvature of said optical body posterior concave surface, and
   a supporting element including:
     a proximal portion connected with the positioning element periphery,
     a distal portion adapted to contact a zonal ligament,
     a supporting element posterior concave surface on one side of said supporting element between said proximal portion and said distal portion, said supporting element posterior concave surface forming a smooth continuation of said positioning element posterior concave surface and having a curvature identical to the curvature of said positioning element posterior concave surface, and
     a supporting element anterior surface on an opposite side of said supporting element between said proximal portion and said distal portion, said supporting element anterior surface having a concavity which has an opposite direction of curvature from said supporting element posterior concave surface, such that said supporting element non-linearly decreases in thickness between said supporting element anterior surface and said supporting element posterior concave surface, from said proximal portion to said distal portion.

2. An intraocular lens as claimed in claim 1, wherein said supporting element has a configuration of a ring.

3. An intraocular lens as claimed in claim 1, wherein said supporting element is comprised of two pairs of diametrically opposite projections, each projection having a proximal portion connected with the positioning element periphery.

* * * * *